United States Patent [19]
Bashour

[11] Patent Number: 5,803,898
[45] Date of Patent: Sep. 8, 1998

[54] INTUBATION SYSTEM

[76] Inventor: Charles Allen Bashour, 2224 Fenwick Rd., University Heights, Ohio 44118-3118

[21] Appl. No.: 850,934

[22] Filed: May 5, 1997

[51] Int. Cl.⁶ ......................................................... A61B 1/22
[52] U.S. Cl. .......................... 600/120; 600/184; 600/143; 600/146
[58] Field of Search ..................................... 600/114, 184, 600/120, 143, 139, 146, 162, 182

[56] References Cited

U.S. PATENT DOCUMENTS

| | | | |
|---|---|---|---|
| 3,610,231 | 10/1971 | Takahashi | 600/146 X |
| 4,601,283 | 7/1986 | Chikama. | |
| 4,624,243 | 11/1986 | Lowery et al. | 600/114 X |
| 5,069,226 | 12/1991 | Yamauchi et al. . | |
| 5,327,881 | 7/1994 | Greene | 600/120 |
| 5,607,386 | 3/1997 | Flam | 600/114 X |
| 5,676,635 | 10/1997 | Levin | 600/146 X |

Primary Examiner—Jeffrey A. Smith
Attorney, Agent, or Firm—David G. Henry

[57] ABSTRACT

The invention is of an intubation system which is based on a specially designed fiberscopic instrument of a new design to address the unique requirements for intubation. The fiberscope (referred to as an "endoscopic stylet" by the inventor) has a largely semi-rigid insertion cord which permits a user to pre-form the endoscopic stylet to follow the anticipated contours of the airway leading to the trachea and to insure that it reliably shepherds the associated endotracheal tube to the intended tracheal position. By visually tracking the progress of the endoscopic stylet through the airway, specifically through the vocal cords and into the trachea, placed at the proper distance above the carina, as permitted by the fiberoptic portions of the endoscopic stylet, proper positioning of the endotracheal tube is virtually assured, and post-intubation verification would be unnecessary in most instances since intubation is itself verification of proper endotracheal tube placement.

2 Claims, 2 Drawing Sheets

INTUBATION SYSTEM

BACKGROUND OF THE INVENTION

1. Field of The Invention

Applicant's invention relates to endoscopy and to instruments and methodologies which are useful in the performance of intubation procedures.

2. Background Information

Intubation is the process by which an endotracheal tube is inserted into the trachea of an individual who requires assistance in breathing. The need for intubation often arises from a cardiac and/or pulmonary arrest, or from trauma when the patient is unable to breath without outside intervention. Alternatively, elective intubation may be involved in preparing a patient for surgery under general anesthesia when the capacity for independent breathing will be interrupted.

Intubation is a well-established procedure for obtaining an artificial airway, but is often difficult for the medical professional, and potentially dangerous (or, at least, ineffective) for the patient. Properly negotiating the anatomy of the pharynx and larynx to ultimately place an endotracheal tube in the trachea for a proper intubation necessarily requires that the endotracheal tube pass through a patient's vocal cords, not a structure that is always visible at the time of intubation, and thus intubation is often a partially blind procedure that relies on imperfect, indirect methods for confirming proper endotracheal tube placement.

A laryngoscope is an instrument held with the left hand during intubation, and is used to divert the patient's tongue and epiglottis, thereby distorting the anatomy to expose the vocal cords. Exposing the vocal cords makes an intubation (where the endotracheal tube must pass through the vocal cords and enter the trachea) at least possible. Often, however, even with the laryngoscope in an optimal position, the vocal cords cannot be visualized due to a small mouth opening, inability to flex the neck due to trauma or other reasons, or an anterior position of the larynx, and, therefore, placement of the endotracheal tube becomes a partially blind procedure. In fact, the most critical phase of intubation is that where the endotracheal tube is seen passing through the vocal cords and into the trachea. Without seeing this, an intubation becomes more difficult and may even be impossible.

In any event, absolute certainty of the proper placement of the endotracheal tube in the trachea is an indispensable requirement of every intubation. Thus, even if the vocal cords can be visualized and the endotracheal tube is seen passing through the vocal cords and into the trachea, indirect methods for verifying proper placement of the endotracheal tube are required to assure that the endotracheal tube is in proper position within the trachea, that being 2.5 to 3.0 cm above the carina.

Methods for insuring proper endotracheal tube placement, and thereby excluding an esophageal intubation (where the endotracheal tube extends into the esophagus, rather than the trachea) are not always reliable. Even the most reliable indirect methods for verifying a tracheal intubation are undesirably time consuming, expensive, and can be associated with incidental risks (such as by radiation exposure).

The most commonly employed indicator for proper placement of an endotracheal tube involves listening to the upper abdomen and chest for breath sounds as the patient is ventilated. Such apparent indications of proper endotracheal tube placement have, however, been reported in cases which ultimately turned out to involve esophageal intubations.

Another indirect method for verifying proper placement of an endotracheal tube involves measuring carbon dioxide emissions from the endotracheal tube (to indicate that the endotracheal tube is in communication with the patient's lungs and, therefore, in a position for exhausting the carbon dioxide of respiration). The carbon dioxide detection method involves the expense of a disposable carbon dioxide sensor, and is susceptible to both "false positives" and "false negatives" under certain circumstances relating to the patient's gastric state and/or cardiac function at the time of intubation.

Another method of determining proper placement of an endotracheal tube is by xray verification. This involves radiation exposure which should be avoided when non-radiation methods are equally efficacious. Moreover, xray verification of proper endotracheal tube placement is time consuming and involves additional expense.

In light of the limitations to indirect, post-intubation indication of proper endotracheal tube placement, it is highly desirable to insure that proper tracheal intubation has occurred in the first place, and even more desirable to confirm proper placement as the intubation is proceeding. Absolute assurance of correct endotracheal tube placement is only possible when the medical professional can actually watch the tube pass through the vocal cords and into the trachea, and see its position in the trachea.

Visualization of the path through which an endotracheal tube must pass in connection with an intubation is known (See *Fiberoptic Endoscopy and the Difficult Airway*, Ovassapian, Andranik (Lippincott-Raven)). However, no existing instrument permits visualization of the intubation process itself, as it proceeds. Also, existing endoscopes are not specifically or exclusively designed for intubation and can be difficult to use by other than highly trained and experienced practitioners of intubations. According to Dr. Ovassapian, two methods for so called fiberoptic endoscopy are presently available: (1) the "tube-first" approach, and (2) the "scope-first" approach.

In the tube-first approach to fiberoptic intubation, an intubating airway (a temporary device that is placed in the patient's mouth to guide an endotracheal tube generally toward its intended target) is placed, and an endotracheal tube is then inserted into the passageway of the intubating airway. While a second person supports the endotracheal tube, which is now held in position by the intubating airway, the fiberscope is advanced (using both hands) through the endotracheal tube through the vocal cords and into the trachea. Using the fiberscope as a guide wire, one of the medical professionals then advances the endotracheal tube over the fiberscope and (hopefully) into the trachea. The long fiberscope insertion cord is then withdrawn while holding the endotracheal tube in place.

The tube-first approach to fiberoptic intubation using presently available apparatuses is not without its limitations. A common problem may occur when the fiberscope is advanced through the endotracheal tube. As the distal tip of the fiberscope nears the distal end of the endotracheal tube, the fiberscope tip may (and often does) pass through the "Murphy's eye" of the endotracheal tube. The Murphy's eye is a lumen which opens through the side of the endotracheal tube near its distal end which is provided for preventing complete blockage of the endotracheal tube, even if the distal opening somehow becomes blocked. When the fiberscope tip does pass though the Murphy's eye, withdrawing the fiberscope after placement of the endotracheal tube is often impossible, unless the endotracheal tube is also withdrawn. Withdrawing the endotracheal tube under these circumstances is, on occasion, impossible without substantial trauma to the patient. Maneuverability of the endotracheal tube/fiberscope combination is severely hampered, and the combined cross sectional dimension of the two entangled items near their terminal ends is substantially larger than can be safely withdrawn from the patient. Whatever the complications associated with this event, precious time is consumed, and the objective of rapidly and accurately establishing, what in many cases is a life saving airway, will be delayed or even prevented. Furthermore, the pliable insertion cord of presently available fiberscopes can be easily displaced by the stiffer endotracheal tube, and the endotracheal tube may, therefore, be placed in the esophagus, even though the fiberoptic scope was initially in the trachea.

In the scope-first approach, the medical professional first attempts to direct the fiberscope, with an endotracheal tube pre-loaded back on the most proximal segment of the insertion cord, fully into the trachea, after which the endotracheal tube is, as described before, advanced over the fiberscope, using the fiberscope essentially as a guide wire, into the trachea. This approach reduces the likelihood of accidentally extending the fiberscope tip through the Murphy's eye of the endotracheal tube, but exacerbates the limitations of the fiberscope to act as a guide wire. The fiberscopes of the prior art are often simply too flexible to reliably act as a guide wire type device for shepherding the endotracheal tube to its intended position in the trachea relative to the carina. This is true, in part, because the fiberscope must, over a longer and more curved path than involved in the tube-first approach, deflect and conform the advancing endotracheal tube, against a certain degree of rigidity of its own, to traverse the pathway to the trachea. A lack of sufficient or moldable rigidity of the fiberscope often makes it quite difficult to direct the fiberscope along the intended pathway, even though the practitioner can see where the fiberscope is going.

In both the tube-first approach and the phases of the scope-first approach, during which the endotracheal tube is advanced over the fiberscope, the distal margins of the endotracheal tube may still impinge on laryngeal anatomy and be incapable of being advanced into the trachea, in part, because the highly flexible fiberscope, even if properly placed, may not be able to resist the deviating forces which act against the endotracheal tube. Also, during any phase of an intubation procedure where one attempts to advance an endotracheal tube over an already-placed fiberscope, there may be a tendency to inadvertently pull the fiberscope back from its proper position as the endotracheal tube is advanced, thereby resulting in an esophageal intubation or other complications. This is true particularly because two practitioners are necessarily involved in presently known fiberoptic intubation procedures, and perfect coordination between the two, to detecting the lack thereof in the often hectic environment of a difficult intubation, for example, is not always possible.

The need for two practitioners for performing fiberoptic endoscopy in the context of intubation procedures arises, in part, from the fact that available fiberscopes and endotracheal tubes are not truly designed to be used together. Presently available fiberscopes include features which are unnecessary for intubation purposes—auxiliary channels for transporting irrigation fluids, for fluid evacuation, or even for biopsy work. Their length far exceeds that of the endotracheal tubes with which they may be used, thus making possible the Murphy's eye entanglement problem described above. As already mentioned, presently available fiberscopes lack a sufficient degree of rigidity to retain a desired configuration which would be most helpful in manipulating the fiberscope and endotracheal tube as one unit and insuring that the fiberscope (and the loaded endotracheal tube) will follow a desired path shape which ends in the trachea. Finally, the complexity of full-function fiberscopic systems (largely the result of unnecessary features for intubation purposes) makes the units difficult to use and the associated intubation unnecessarily difficult to complete.

It would well serve medical professionals and their patients to have available a single device which addresses the deficiencies of equipment which is presently used to perform intubation, and could be employed using the standard hand motions that are generally well known by most practitioners who perform routine intubations. The effect would be to simplify intubation and thereby increase the probability that each intubation will proceed properly, swiftly, and safely.

The beneficial characteristics of an improved intubation system would arise from a uniquely configured fiberscope. The fiberscope would be of a new design, compared to currently known fiberscopes, and includes an insertion cord which is configured to prevent extension of its distal tip beyond the distal end of an endotracheal tube fitted thereon. To enhance the directional control of the fiberscope (e.g. enabling the direct translation of the user's hand movements to the distal portions of the fiberscope), and to bolster its ability to pass anatomical features which would otherwise tend to divert the fiberscope in an undesirable direction, or interfere with the endotracheal tube's following of the fiberscope, the insertion cord would be modified from currently available examples. The insertion cord would include a malleable, rigidity enhancing member which will endow it both with the rigidity which is desirable to aid in controllably advancing the cord along its intended path and the shape memory which will allow the user to form segments of its length to conform to the pathway which it must traverse during the intubation. In the absence of irrigation and evacuation channels and similar unnecessary features of present fiberscope models, the newly designed fiberscope would be easier to clean and maintain, and likely be available at a lower cost. It could also be made to exhibit a smaller cross section and thus be suitable for a wider range of endotracheal tube sizes, including those for pediatric use.

The fiberscope, designed according to the present invention, is what might better be described as an endotracheal tube "Endoscopic Stylet Endotracheal Tube" for it serves both functions of a fiberoptic endoscope for visualization and manipulation of the intubation procedure and those of a stylet to help conform the endotracheal tube to any configuration for somewhat forcibly advancing the apparatus along a desired path, even against resistance from existing anatomical features. Because of these features, and the fact that the endoscopic stylet and its intended endotracheal tube mate would be of approximate equal length and designed for use, relative to each other, as static components a single unit during an intubation procedure, the system would be used by a single practitioner. Adding the feature of an remotely-controlled, articulating terminal segment for the insertion cord of the endoscopic stylet would enable the practitioner to maneuver the distal end of the associated endotracheal tube which is fitted thereon, thus further enhancing the ease of use and reliability of the endoscopic stylet system.

No existing instrument allows its user to visualize the precise position of the distal end of the endotracheal tube relative to surrounding anatomy as the endotracheal tube is being placed, and, by manipulating the end of the insertion cord, directly affect the orientation of the distal endotracheal tube end, and thereby guide the endotracheal tube through the vocal cords.

More specific features of the intubation system of the present invention will be disclosed in the Detailed Description of the Preferred Embodiment. In sum, however, the endoscopic stylet system of the present invention: (1) facilitates simultaneous advancement of the terminal end of an endotracheal tube and of a fiberscopic instrument for visualization of such advancement; (2) permits independent use by a single practitioner by eliminating unnecessary system bulk and fiberscope insertion cord length; (3) substantially reduces likelihood of esophageal intubations and of Murphy's eye entanglement complications; (4) affords its users remote controllability of the terminal segments of the endotracheal tube for ease of maneuvering through action of the associated, remotely controllable segment of the fiberscopic stylet; (5) affords greatly enhanced directional control of the distal portions of the fiberscope; (6) facilitates the negotiation of anatomical features which would otherwise tend to divert the fiberscope in an undesirable direction, or interfere with the endotracheal tube's following of the fiberscope; and (7) eliminates inadvertent mis-direction of a previously, properly-placed fiberscope as in the case of presently practiced procedures where an endotracheal tube is independently advanced over the fiberscope.

SUMMARY OF THE INVENTION

It is an object of the present invention to provide a novel instrumental system for the performing intubation procedures.

It is another object of the present invention to provide an instrumental system for performing intubation procedures, which system obviates complications associated with the use of presently available fiberscopic instruments for intubation procedures.

It is another object of the present invention to provide an instrumental system for performing intubation procedures, which system obviates the complexity, risks and potential delays associated with "tube-first" or "scope-first" procedures of the prior art.

It is another object of the present invention to provide an instrumental system for performing intubation procedures, which system virtually insures that an esophageal intubation will not have occurred at the end of the placement phase of the procedure.

It is another object of the present invention to provide an instrumental system for performing intubation procedures, which system simplifies the intubation procedure by combining stylet or guide wire type functions with the fiberscopic instrument for diverting or managing anatomical structures which would otherwise impede progress of the fiberscope and permitting the advancement and manipulation, as a unit, of both the fiberscopic and endotracheal tube components of the system using the same hand motions as are presently known to most practitioners who perform intubations.

It is another object of the present invention to provide an instrumental system for performing intubation procedures which allows its user to visualize the precise position of the distal end of the endotracheal tube relative to surrounding anatomy, and, by manipulating the end of the insertion cord, directly affect the orientation of the distal endotracheal tube end, and thereby guide the endotracheal tube through the vocal cords to a proper position in the trachea.

It is another object of the present invention to provide an instrumental system for performing intubation procedures, which system directly verifies proper placement of an endotracheal tube, not after intubation, but simultaneously with intubation, thus eliminating wasted time, expense, and/or radiation exposure involved with presently employed indirect methods as well as virtually any chance of an improperly placed endotracheal tube during an intubation procedure.

It is another object of the present invention to provide an instrumental system for performing intubation procedures, which system includes a fiberscopic type instrument which is specifically sized and configured to correspond to the length of an endotracheal tube with which the fiberscopic instrument will be used, such that there is little excess insertion tube length to manage during an intubation, and little, if any, danger of engaging the distal tip of the fiberscopic instrument with the Murphy's eye of the endotracheal tube.

In satisfaction of these and related objectives, Applicant's present invention provides an intubation system which is based on newly designed fiberscope design. The endoscopic stylet of the present invention is designed to serve, not only as the means for transmitting a visual image of the anatomical surfaces of the areas through and to which its distal tip passes during an intubation procedure, but to serve as a semi-rigid stylet which may be formed into, and hold, a shape for conforming generally to the contour of the pathway past which the instrument must pass during the procedure. In addition to making its passage through the desired pathway easier because of the option for pre-forming its shape to correspond to the anticipated pathway contours, this semi-rigidity characteristic of the "endoscopic stylet" of the present invention serves the functions of: (1) a stylet for diverting anatomical features, such as the tongue which might (even with the help of a laryngoscope) otherwise obstruct the intubation procedure; and (2) a guide structure for an endotracheal tube which helps prevent a diversion of the endotracheal tube from the course defined by the endoscopic stylet into the trachea, even as against diversionary forces applied by unfavorable upper airway anatomy (such as a posteriorly displaced epiglottis due to lymphoid tissue), or by soft tissue edema, tumors, or unusually pronounced fatty deposits.

The features designed into the endoscopic stylet of the present invention, individually and collectively, were selected specifically for their utility in performing intubation procedures. Absent from the endoscopic stylet are features which have no utility for intubations, and, in fact, may hinder the procedure. Such features include excessive insertion cord length, the one or more working channels, integral suction and irrigation systems, cauterizing tips, etc. which are found in many non-intubation specific fiberscopic instruments.

Benefits of this selection of features exceed the readily apparent. The cross sectional size of the insertion cord of the present endoscopic stylet may, for example, be smaller for accommodating even the smallest endotracheal tubes with which the instrument might be used. Also, by not merely adding features, but eliminating unnecessary ones, the present instrument is a more cost effective choice for intubation procedures than instruments of old design. Further, by reducing the instrument's bulk and complexity, one expands the group of medical professionals who will more readily be able to use the instrument from that relatively small group who are qualified to use presently available endoscopic instruments. The latter two points—cost savings and simplicity of use and operation—could well translate into saved lives, as the instrument might well be found in environments which traditional endoscopic instruments would never be placed, such as with paramedical field personnel. Further still, cleaning and maintenance of the endoscopic stylet (without unnecessary and difficult-to-clean working channels) is much less time-consuming than instruments of the prior art.

The endoscopic stylet is provided with a remotely deflectable tip portion. The semi-rigid proximal and middle portions of the insertion cord of the endoscopic stylet greatly facilitate maneuvering the distal tip, past the anatomy of the mouth and throat, into position near the vocal cords. Once in this position, the user actuates the deflectable tip to orient it for easy passage through the vocal cords and into the trachea. Because the endotracheal tube of the present system is intended to be loaded on the endoscopic stylet during the entirety of the insertion phase of an intubation procedure, and the terminal end of the endotracheal tube is substantially coextensive with that of the endoscopic stylet, deflecting the tip portion of the endoscopic stylet effects a like deflection of the distal portion of the endotracheal tube. The endoscopic stylet and the associated endotracheal tube as a single unit become highly maneuverable by one practitioner using the right hand, while the left hand is maintaining the best possible exposure by placing the laryngoscope in the standard position. Thus, the hand motions involved are at least very similar to those already known and employed by most practitioners performing standard endotracheal intubations, aided only by a stylet that puts the operator's eye at the distal end of the endotracheal tube, and gives the operator the ability to flex and rotate the endotracheal tube tip.

The endoscopic stylet is configured to correspond to the length of endotracheal tubes with which the instrument will be used, thereby eliminating such excess insertion cord length as would prevent the effective single-handed use of the instrument if it shared length-wise dimensions of typical fiberscopes of the prior art. The handle member, which includes the eye piece for viewing images transmitted from the distal tip of the endoscopic stylet and thumb controls for manipulating the divertable distal portion of endoscopic stylet, is compact and situated immediately proximal to the position of a loaded endotracheal tube. This means that the user can operate the endoscopic stylet and endotracheal tube as a single unit duplicating hand motions that are already known as standard intubation techniques by most practitioners. The practitioner need only use the right hand to manipulate the endoscopic stylet, leaving the left hand to maintain exposure with the laryngoscope. This obviates the need for a second practitioner.

The substantial correspondence between the length of the insertion cord of the endoscopic stylet with that of the endotracheal tube reduces the possibility of the endoscopic stylet tip passing through and lodging in the Murphy's eye of the endotracheal tube. Also, because of the stylet characteristics of the endoscopic stylet, there is no need for using an intubating airway, a separate stylet or guide wire, and no need for performing either a "tube-first" or "scopefirst" type procedure with the inherent delays and chances for esophageal intubations. Finally, because the user is visually monitoring the progress of the endotracheal tube as it progresses toward and through the patient's vocal cords, there is no need for intubation verification. The real-time visual verification of the endoscopic stylet, which necessarily carries with it the distal portion of the endotracheal tube as it passes through the vocal cords and into the trachea, insures a proper endotracheal tube placement in every instance. One merely needs to insure that the endotracheal tube not be inadvertently withdrawn as the endoscopic stylet is withdrawn at the end of the placement phase of an intubation, just as this is necessary as a stylet is withdrawn during a standard intubation.

DETAILED DESCRIPTION OF THE PREFERRED EMBODIMENT

Figure 1:
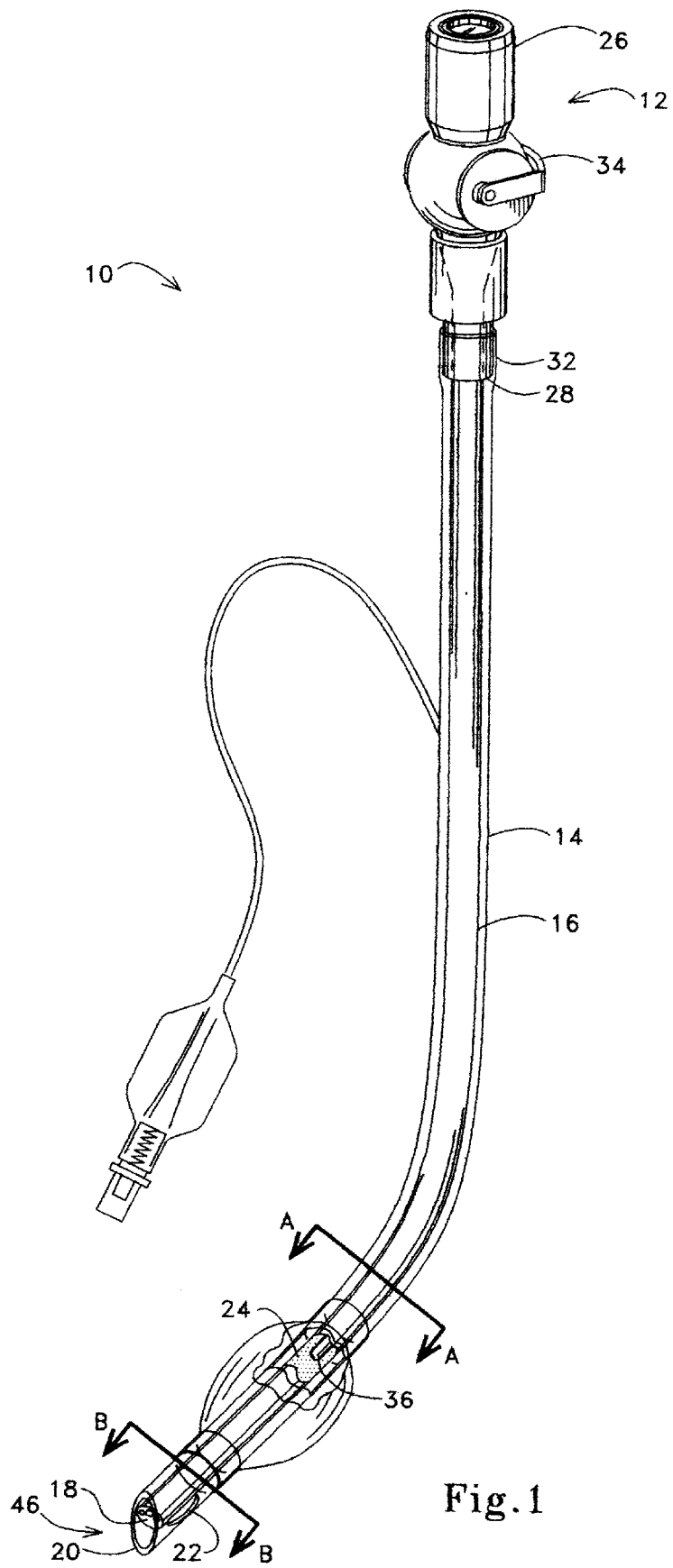
FIG. 1 is a perspective view of the intubation system of the present invention.

Referring to FIG. 1, the intubation system of the present invention is identified generally by the reference numeral 10. System 10 includes an endoscopic stylet 12 on which is fitted an endotracheal tube 14 when system 10 is configured for use. Endoscopic stylet 12 includes an insertion cord 16 which is of a length such that the distal insertion cord tip 18 extends no further than the distal endotracheal tube tip 20 of the endotracheal tube 14 when fitted on the insertion cord 16. This correlation between the lengths of the endotracheal tube 14 and insertion cord 16 effectively prevents accidental passage of the distal insertion cord tip 18 through the Murphy's eye 22 of the endotracheal tube 14.

A terminal segment 24 of the insertion cord 16 of the endoscopic stylet 12 is remotely deflectable using thumb controls 34 which are positioned adjacent to the handle/eye piece 26. Remotely deflectable fiberscope tips and the component mechanisms thereof are known in the art and need not be discussed here for enabling disclosure purposes (see U.S. Pat. No. 3572325 issued to Bazell). However, the combination of the deflectable tip feature and the other characteristics of the present system (the shorter insertion cord 16, for example) and the associated methodology afford benefits which are not readily apparent to the casual observer.

Because the present method teaches inserting the insertion cord 16 with the endotracheal tube 14 loaded thereon, and because the lengths of the insertion cord 16 and the endotracheal tube 14 are matched whereby their respective distal termini are substantially coincident, any deflection of the distal insertion cord tip 18 should, and, in the case of the present system, will, effect a similar deflection of the corresponding portion of the endotracheal tube 14. Thus, a user is able literally to maneuver the distal portions of the endotracheal tube 14 through use of the thumb controls 34 on handle/eye piece 26. This is in contrast to devices of the prior art.

Experimentation by the present inventor has revealed that fiberscopes of old design and configuration cannot provide this benefit. Because the insertion cords of the prior art are so long, it has been found impossible to maneuver the distal portions of an endotracheal tube 14 when aligned with the distal tip of a conventional fiberscope with deflectable tip features. The expanse over which the control wires extend so dampens the mechanical action of the thumb controls, that the inventor was not able to effectively deflect the distal portion of an endotracheal tube by actuating the thumb controls of the conventional fiberscope. Inadequate force is transmitted to the distal tips of these fiberscopes to deflect the endotracheal tube.

In the preferred embodiment of intubation system 10, the handle/eye piece 26 of the endoscopic stylet 12 is situated at the proximal end 28 of the insertion cord 16 which closely corresponds to the proximal end 32 of the endotracheal tube 14. This is in stark contrast to the relative placement of the handle/eye piece of conventional fiberscopes in which, because of a great excess in cord length for the fiberscope, the handle/eye piece is greatly separated from the position of the proximal end of the endotracheal tube during an intubation. In addition, the handle/eye piece 26 of the present system 10 is incorporated into a much more compact unit than comparable structures in conventional fiberscopes—this due to the relative simplicity of endoscopic stylet 12 of the intubation system 10 as will be explained hereafter.

The compact structure of the endoscopic stylet 12 (the combined product of the corresponding lengths of the endotracheal tube 14 and insertion cord 16, and of a more compact, simple handle structure) greatly facilitates handling and fine control of the system 10 during intubation. Existing units have a great excess of fiberscope insertion cord length and can be unwieldy by most accounts and require two handed operation. The endoscopic stylet 12 of the present invention may be confidently manipulated with a single hand (the right), and the terminal segment 24 can be controlled using thumb controls 34.

Figure 2:
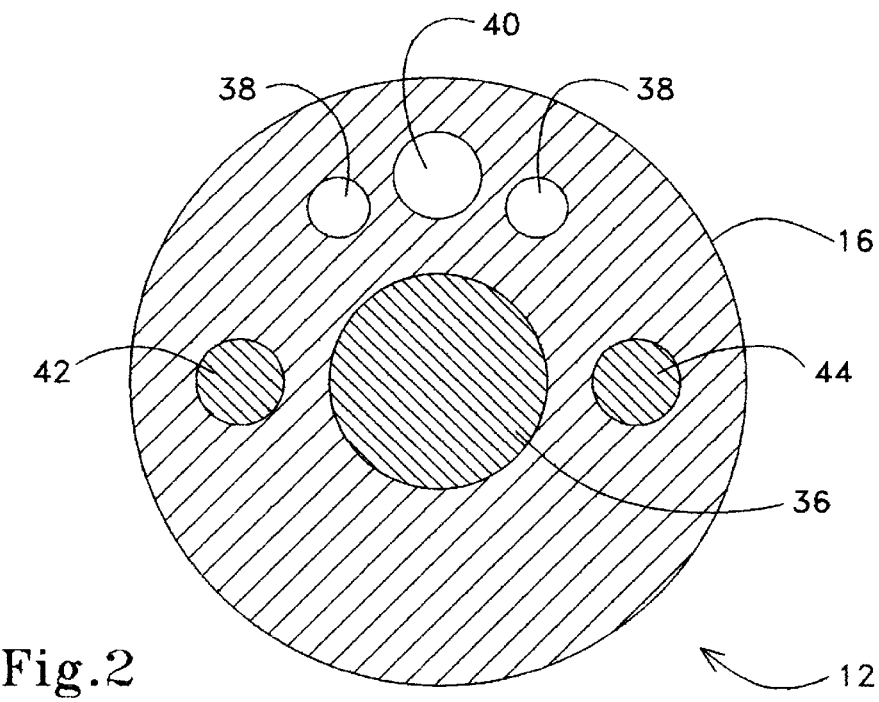
FIG. 2 is a cross sectional view of the insertion cord of the endoscopic stylet shown in FIG. 1 along Line A—A.
Figure 3:
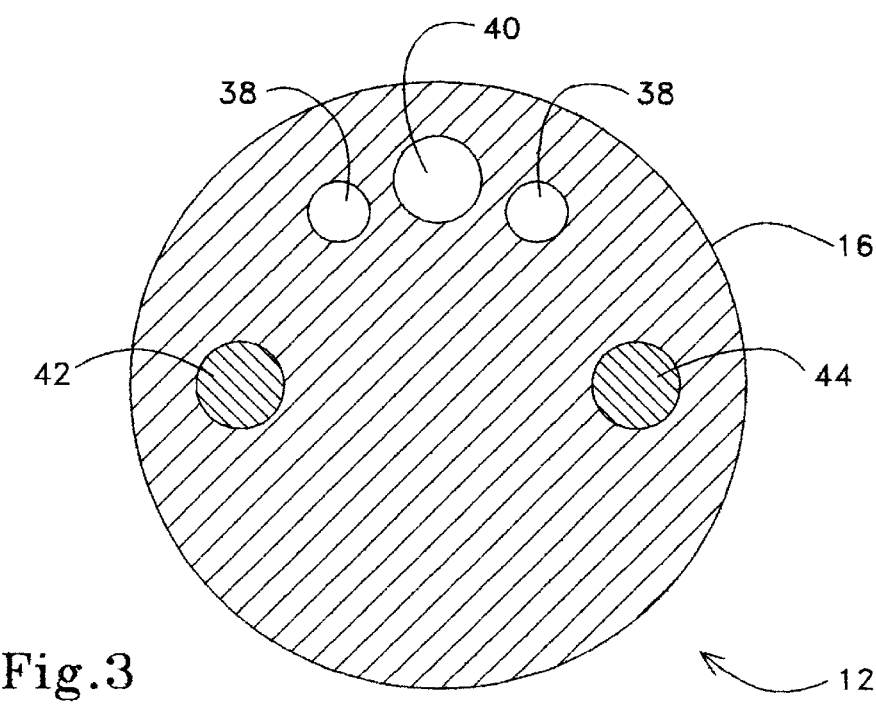
FIG. 3 is a cross sectional view of the insertion cord of the endoscopic stylet shown in FIG. 1 along Line B—B.

Referring to FIGS. 2 and 3, cross sectional views of the insertion cord 16 of the endoscopic stylet 12 at the two indicated sites shows a relatively simple structure. Extending through the length of the insertion cord 16 from the handle/eye piece 26 to a point near (but not to) the proximal end of the terminal segment 24 is an elongate rigidity member 36. Rigidity member 36 is, in the preferred embodiment, a yieldable, shape-retaining metallic rod which endows the insertion cord 16, and, therefore, the loaded endotracheal tube 14, with the capacity for retaining curvature formed by its user prior to insertion during an intubation in order to conform to the contour of the path which it must traverse during an intubation. The rigidity member 36 extends, in the preferred embodiment, from approximately the proximal end of the insertion cord 16 to a point proximal to the distal insertion cord tip 18, not inclusive of the remotely deflectable terminal segment 24. The result is an insertion cord 16 and endotracheal tube 14, the majority of the length of which (the "semi-rigid segment") holds a desired shape for diverting anatomical features, such as the tongue, which could otherwise impede the intubation procedure.

Also visible from the cross sectional views of FIGS. 2 and 3 are the light guide cables 38, fiberoptic bundle 40, and control wires 42 and 44. Light guide cables 38 are a conventional feature for fiberscopes, and in this case carries light from a light source (not depicted in the drawings) in or near handle/eye piece 26 to the distal tip 46 of the endoscopic stylet 12 for providing light in the area to which the insertion cord 16 is extended during an intubation procedure. Control wires 42 and 44 are connected between thumb controls 34 in the handle/eye piece 26 and the deflection mechanisms in the terminal segment 24 of the insertion cord 16 generally according to conventional design for such mechanisms. The fiberoptic bundle 40 is the group of fiberoptic fibers which carry images from the distal tip 46 of the insertion cord 16 to the optics of handle/eye piece 26.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. An intubation system comprising:

a fiberscope having a handle/eye piece member attached to an elongate insertion cord, said insertion cord having a proximal insertion cord end which is attached to said handle/eye piece member, and a distal insertion cord end, an elongate rigidity member being encased within said insertion cord and extending within said insertion cord substantially from said proximal insertion cord end through a semi-rigid segment of said insertion cord, said rigidity member being fashioned from a shape memory material;

an endotracheal tube having a length which is approximately equal to the length of said insertion cord of said fiberscope between the juncture of said handle/eye piece member and said insertion cord and said distal insertion cord end, said endotracheal tube having an interior diameter sufficient for telescopic reception of said insertion cord therethrough.

2. The intubation system of claim 1 wherein said fiberscope further includes remote deflection means for deflecting a distal segment of said insertion cord through actuation of control means associated with said handle/eye piece member attached to said deflection means by control wires extending through said insertion cord from said handle/eye piece member.

* * * * *